(12) United States Patent
Garcon et al.

(10) Patent No.: US 6,791,014 B2
(45) Date of Patent: Sep. 14, 2004

(54) USE OF HPPD INHIBITORS AS SELECTION AGENTS IN PLANT TRANSFORMATION

(75) Inventors: Frédéric Garcon, Lyons Cedex (FR); Bernard Pelissier, St. Didier Au Mont D'Or (FR)

(73) Assignee: Aventis Cropscience, S.A. (FR)

( * ) Notice: Subject to any disclaimer, the term of this patent is extended or adjusted under 35 U.S.C. 154(b) by 13 days.

(21) Appl. No.: 09/921,263

(22) Filed: Aug. 2, 2001

(65) Prior Publication Data

US 2002/0100076 A1 Jul. 25, 2002

(30) Foreign Application Priority Data

Aug. 11, 2000 (FR) ............................................. 00 10601

(51) Int. Cl.$^7$ ........................ C12N 5/14; C12N 15/52; C12N 15/82; A01H 4/00; A01H 5/00
(52) U.S. Cl. ....................... 800/298; 800/278; 800/288; 800/300; 435/419; 435/425; 435/426; 435/427; 435/429; 435/430.1; 435/418
(58) Field of Search ................................ 435/419, 425, 435/427, 429, 418, 410, 413, 415, 426, 430.1, 431; 800/300, 278, 295, 298, 312; 536/23.1, 23.6

(56) References Cited

U.S. PATENT DOCUMENTS

| | | | |
|---|---|---|---|
| 4,443,971 A | * 4/1984 | Chaleff | 47/58 |
| 5,073,675 A | 12/1991 | Jones et al. | 800/205 |
| 5,217,902 A | 6/1993 | Jones et al. | 435/320.1 |
| 6,245,968 B1 | * 6/2001 | Boudec | 800/278 |

FOREIGN PATENT DOCUMENTS

| | | |
|---|---|---|
| AU | 718982 | 12/1996 |
| WO | WO 96/38567 | 12/1996 |
| WO | WO 99/24585 A | 5/1999 |
| ZA | 98/10076 | 7/1999 |

OTHER PUBLICATIONS

Chaleff R. et al. UCLA Symposium, Steamboat Springs, Mar. 30–Apr. 6, 1986.*

* cited by examiner

*Primary Examiner*—David T. Fox
*Assistant Examiner*—Russell Kallis
(74) *Attorney, Agent, or Firm*—Connolly Bove Lodge & Hutz LLP (57) ABSTRACT

The present invention provides a method for transforming plants cells by introducing a heterologous gene into competent plant cells with a gene for tolerance to HPPD inhibitors as a selection marker wherein a step for bleaching the competent plant cells is carried out prior to transforming the cells by introducing a suitable amount of HPPD inhibitor into the cell culture medium. The invention also provides methods for preparing transgenic plants comprising a heterologous gene.

17 Claims, 2 Drawing Sheets

SEQUENCE LISTING

<160> NUMBER OF SEQ ID NOS: 2

<210> SEQ ID NO 1
<211> LENGTH: 5281
<212> TYPE: DNA
<213> ORGANISM: Artificial sequence
<220> FEATURE:
<223> OTHER INFORMATION: Artificial sequence description: chimeric gene

<400> SEQUENCE: 1

```
ctagtggcgc cacgcgtgat atcatgcatg ttaacatcga tccatgggcg cgccttaatt      60
aaatttaaat cagctgcatt aatgaatcgg ccaacgcgcg gggagaggcg gtttgcgtat     120
tgggcgctct tccgcttcct cgctcactga ctcgctgcgc tcggtcgttc ggctgcggcg     180
agcggtatca gctcactcaa aggcggtaat acggttatcc acagaatcag gggataacgc     240
aggaaagaac atgtgagcaa aaggccagca aaaggccagg aaccgtaaaa aggccgcgtt     300
gctggcgttt ttccataggc tccgcccccc tgacgagcat cacaaaaatc gacgctcaag     360
tcagaggtgg cgaaacccga caggactata aagataccag gcgtttcccc ctggaagctc     420
cctcgtgcgc tctcctgttc cgaccctgcc gcttaccgga tacctgtccg cctttctccc     480
ttcgggaagc gtggcgcttt ctcatagctc acgctgtagg tatctcagtt cggtgtaggt     540
cgttcgctcc aagctgggct gtgtgcacga accccccgtt cagcccgacc gctgcgcctt     600
atccggtaac tatcgtcttg agtccaaccc ggtaagacac gacttatcgc cactggcagc     660
tgccactggt aacaggatta gcagagcgag gtatgtaggc ggtgctacag agttcttgaa     720
gtggtggcct aactacggct acactagaag gacagtattt ggtatctgcg ctctgctgaa     780
gccagttacc ttcggaaaaa gagttggtag ctcttgatcc ggcaaacaaa ccaccgctgg     840
tagcggtggt ttttttgttt gcaagcagca gattacgcgc agaaaaaaag gatctcaaga     900
agatcctttg atcttttcta cggggtctga cgctcagtgg aacgaaaact cacgttaagg     960
gattttggtc atgagattat caaaaaggat cttcacctag atcctttaa attaaaaatg    1020 aagttttaaa tcaatctaaa gtatatatga gtaaacttgg tctgacagtt accaatgctt    1080
aatcagtgag gcacctatct cagcgatctg tctatttcgt tcatccatag ttgcctgact    1140
ccccgtcgtg tagataacta cgatacggga gggcttacca tctggcccca gtgctgcaat    1200
gataccgcga gacccacgct caccggctcc agatttatca gcaataaacc agccagctgg    1260
aagggccgag cgcagaagtg gtcctgcaac tttatccgcc tccatccagt ctattaattg    1320
ttgccgggaa gctagagtaa gtagttcgcc agttaatagt ttgcgcaacg ttgttgccat    1380
```

-continued

```
tgctacaggc atcgtggtgt cacgctcgtc gtttggtatg gcttcattca gctccggttc    1440
ccaacgatca aggcgagtta catgatcccc catgttgtgc aaaaaagcgg ttagctcctt    1500
cggtcctccg atcgttgtca gaagtaagtt ggccgcagtg ttatcactca tggttatggc    1560
agcactgcat aattctctta ctgtcatgcc atccgtaaga tgcttttctg tgactggtga    1620
gtactcaacc aagtcattct gagaatagtg tatgcggcga ccgagttgct cttgcccggc    1680
gtcaatacgg gataataccg cgccacatag cagaacttta aaagtgctca tcattggaaa    1740
acgttcttcg gggcgaaaac tctcaaggat cttaccgctg ttgagatcca gttcgatgta    1800
acccactcgt gcacccagct gatcttcagc atctttttact ttcaccagcg tttctgggtg    1860
agcaaaaaca ggaaggcaaa atgccgcaaa aaagggaata agggcgacac ggaaatgttg    1920
aatactcata ctcttccttt tcaatatta ttgaagcatt tatcagggtt attgtctcat    1980
gagcggatac atatttgaat gtatttagaa aaataaacaa ataggggttc gcgcacatt    2040
tccccgaaaa gtgccacctg acgcgccctg tagcggcgca ttaagcgcgg cgggtgtggt    2100
ggttacgcgc agcgtgaccg ctacacttgc cagcgcccta cgcccgctc ctttcgcttt    2160
cttcccttcc tttctcgcca cgttcgccgg ctttccccgt caagctctaa atcgggggct    2220
cccttaggg ttccgattta gtgctttacg gcacctcgac cccaaaaaac ttgattaggg    2280
tgatggttca cgtagtgggc catcgccctg atagacggtt tttcgccctt tgacgttgga    2340
gtccacgttc tttaatagtg gactcttgtt ccaaactgga acaacactca accctatctc    2400
ggtctattct tttgatttat aagggatttt gccgatttcg gcctattggt taaaaaatga    2460
gctgatttaa caaaaattta acgcgaattt taacaaaata ttaacgctta caatttccat    2520
tcgccattca ggctgcgcaa ctgttgggaa gggcgatcgg tgcgggcctc ttcgctatta    2580
cgccagctgg gcaactgttg ggaagggcga tcggtgcggg cctcttcgct attacgccag    2640
ctggcgaaag ggggatgtgc tgcaaggcga ttaagttggg taacgccagg gttttcccag    2700
tcacgacgtt gtaaaacgac ggccagtgaa ttgcggccgc aattcccgat ctagtaacat    2760
agatgacacc gcgcgcgata atttatccta gtttgcgcgc tatattttgt tttctatcgc    2820
gtattaaatg tataattgcg ggactctaat cataaaaacc catctcataa ataacgtcat    2880
gcattacatg ttaattatta catgcttaac gtaattcaac agaaattata tgataatcat    2940
cgcaagaccg gcaacaggat tcaatcttaa gaaactttat tgccaaatgt ttgaacgatc    3000
ggggaaattc gtcgagtcac cctcggccgg gcttttttgac gcttaatcgg cggtcaatac    3060
accacgacgc acctggtcac gttcgatgga ctcgaacagc gccttgaagt tccactcgcc    3120
aaacccatcg tcgcccttgc gctggatgaa ttcgaagaac accgggccca tcagggtttc    3180
cgagaagatc tgcagcagca ggcgtttgtc gccttccacg gaagatccgt ccagcaggat    3240
accgcgtgcc tgcagttgat ccaccggctc gccgtggtca ggcaggcggc cttcgagcat    3300
ttcgtaataa gtgtctggcg gcgcggtcat gaagcgcatg ccgattttct tcaacgcgtc    3360
ccaggtcttg accaggtcgt cggtgaggaa cgccacgtgc tggatgcctt cgccgttgaa    3420
ctgcatcagg aactcttcga tctgccccgc gcccttggac gactcttcgt tcagcgggat    3480
gcggatcatg ccgtccggcg cactcatggc cttggaagtc aggccggtgt actcgccctt    3540
gatatcgaag taacgcgctt cacggaagtt gaacaatttc tcgtagaagt tggcccagta    3600
gaccatgcgg ccgcgataga cgttgtgggt caggtggtcg atgactttga gacctgcacc    3660
gaccggattg cgctccacac cttcgaggta cacgaagtcg atgtcgtaga tcgagctgcc    3720
```

| | | | | |
|---|---|---|---|---|
| ttcgccgaaa | cggtcgatca | ggtacaacgg | cgcgccgccg | atgcccttga tcgccggcag | 3780 |
| gttcaattcc | atcggcccgg | tgtcaatatg | gatcggctgg | gcgccgagtt ccagggcgcg | 3840 |
| gttgtaggcc | ttttgcgagt | ccttcacgcg | gaacgccatg | ccgcacaccg acgggccgtg | 3900 |
| ttcggccgca | aagtaggagg | cgatgctgtt | gggctcgttg | ttgaggatca ggttgatctc | 3960 |
| gccctggcgg | tacaggtgca | cgttcttgga | acggtgggtc | gcgactttgg tgaagcccat | 4020 |
| gatctcgaag | atcggctcca | gggtacccgg | cgtcggcgac | gcgaattcga tgaattcaaa | 4080 |
| gcccatcagg | cccattgggt | tttcgtatag | atctgccatg | caccggatcc ttccgccgtt | 4140 |
| gctgacgttg | ccgaggcttc | tggaggacg | gcgggcgacg | gggaggctgg cggtggactt | 4200 |
| gagcccctgg | aacggagcga | cggcggtggc | cgacgaggcc | atcatcacgg tgggcgccat | 4260 |
| tgacagcggc | ggcaggtacg | acagcgtctc | gaacttcttg | ttgccgtagg ccggccacac | 4320 |
| ctgcatatat | tgaactcttc | caccgttgct | gggaagggtg | gagaagtcgt tagccttctt | 4380 |
| ggtggtgggg | aaggcggcgt | tggacttaag | gccggtgaac | ggagccacca tgttggcctg | 4440 |
| agcaggggcg | gtccggctaa | cggtcgcgac | tgaggaggag | atcgaagcca tggctgcctg | 4500 |
| gctgcctagt | atgtatgtac | tcgctgcttg | cttgggaatt | cgatggtcga gaatccaatg | 4560 |
| agtgacttta | gtgattatga | gctgtatata | taatacttgt | acatgagctg cctgccatcc | 4620 |
| aacggataaa | aacaaatcta | tcttaacttg | tagtgattct | gagcgtagga tgttgtggct | 4680 |
| cttggaattt | catgcatagt | gtccacataa | tataattgca | atttgaagac cttatcatat | 4740 |
| agccaccaga | aatggagagc | cacgtgtcaa | atgcacattg | ctcaaaatat cttatctcat | 4800 |
| cttctaaagg | agaggtagac | atggaagggt | cggagggtga | gtgtaatttt tatgaatcat | 4860 |
| gaggttaata | gtgtgtggtt | tatattgtta | atgtttttaac | tatcatgagc gtttgaaaat | 4920 |
| ctgctaccgt | aattaagtag | cagatgtgtt | atttttcatc | cacatcccgt cacattgcct | 4980 |
| ataatcaaaa | agagtttcaa | aaattaccta | aaaccatgt | aaattctttg aaacctaccg | 5040 |
| aaattctaaa | aagaaaatat | tgatatcaaa | atacgtgaaa | actggaccaa tattacccga | 5100 |
| aactggacca | atatgttgta | gtgtggttga | gccgctattg | ataagtagtc tagtgctttt | 5160 |
| aatagtaagg | ttggaattat | taaagcataa | ataaaaaaca | aatacaaata caaatttatt | 5220 |
| aagactagaa | aaattgtatc | atccaagtat | tgaattatct | agaggatccc cgggggatcc | 5280 |
| a | | | | | 5281 |

<210> SEQ ID NO 2
<211> LENGTH: 5909
<212> TYPE: DNA
<213> ORGANISM: Artificial sequence
<220> FEATURE:
<223> OTHER INFORMATION: Artificial sequence description: chimeric gene

<400> SEQUENCE: 2

| | | | | |
|---|---|---|---|---|
| ggtggcggcc | gctctagagc | ttgcatgcct | gcaggtcgag | gagaaatatg agtcgaggca | 60 |
| tggatacact | aagttcccct | gaagtgagca | tgatctttga | tgctgagatg attcccagag | 120 |
| caagatagtt | tgtgctgcaa | gtgacacaat | tgtaatgaaa | ccaccactca acgaatttac | 180 |
| ttgtggcttt | gacatgtcgt | gtgctctgtt | tgtatttgtg | agtgccggtt ggtaattatt | 240 |
| tttgttaatg | tgattttaaa | acctcttatg | taaatagtta | ctttatctat tgaagtgtgt | 300 |
| tcttgtggtc | tatagtttct | caaagggaaa | ttaaaatgtt | gacatcccat ttacaattga | 360 |
| taacttggta | tacacaaact | ttgtaaattt | ggtgatattt | atggtcgaaa gaaggcaata | 420 |
| cccattgtat | gttccaatat | caatatcaat | acgataactt | gataatacta acatatgatt | 480 |

-continued

| | |
|---|---|
| gtcattgttt ttccagtatc aatatacatt aagctactac aaaattagta taaatcacta | 540 |
| tattataaat cttttttcggt tgtaacttgt aattcgtggg ttttttaaaat aaaagcatgt | 600 |
| gaaaattttc aaataatgtg atggcgcaat tttattttcc gagttccaaa atattgccgc | 660 |
| ttcattaccc taatttgtgg cgccacatgt aaaacaaaag acgattctta gtggctatca | 720 |
| ctgccatcac gcggatcact aatatgaacc gtcgattaaa acagatcgac ggtttataca | 780 |
| tcatttttatt gtacacacgg atcgtatgat tgtcattgtt tttccagtat caatatacat | 840 |
| taagctacta caaaattagt ataaatcact atattataaa tcttttttcgg ttgtaacttg | 900 |
| taattcgtgg gttttttaaaa taaaagcatg tgaaaatttt caaataatgt gatggcgcaa | 960 |
| ttttattttc cgagttccaa aatattgccg cttcattacc ctaatttgtg cgccacatg | 1020 |
| taaaacaaaa gacgattctt agtggctatc actgccatca cgcggatcac taatatgaac | 1080 |
| cgtcgattaa aacagatcga cggtttatac atcatttttat tgtacacacg gatcgatatc | 1140 |
| tcagccgtta gatttaatat gcgatctgat tgctcaaaaa atagactctc cgtctttgcc | 1200 |
| tataaaaaca atttcacatc tttctcaccc aaatctactc ttaaccgttc ttcttcttct | 1260 |
| acagacatca atttctctcg actctagaat tcgaaacaca acatatacaa aacaaacgaa | 1320 |
| tctcaagcaa tcaagcattc tacttctatt gcagcaattt aaatcatttc ttttaaagca | 1380 |
| aaagcaattt tctgaaaatt ttcaccattt acgaacgata gccatggctt cgatctcctc | 1440 |
| ctcagtcgcg accgttagcc ggaccgcccc tgctcaggcc aacatggtgg ctccgttcac | 1500 |
| cggccttaag tccaacgccg ccttcccccac caccaagaag gctaacgact ctccaccct | 1560 |
| tcccagcaac ggtggaagag ttcaatatat gcaggtgtgg ccggcctacg caacaagaa | 1620 |
| gttcgagacg ctgtcgtacc tgccgccgct gtctatggcg cccaccgtga tgatggcctc | 1680 |
| gtcggccacc gccgtcgctc cgttccaggg gctcaagtcc accgccagcc tccccgtcgc | 1740 |
| ccgccgctcc tccagaagcc tcggcaacgt cagcaacggc ggaaggatcc ggtgcatggc | 1800 |
| agatctatac gaaaacccaa tgggcctgat gggctttgaa ttcatcgaat tcgcgtcgcc | 1860 |
| gacgccgggt accctggagc cgatcttcga gatcatgggc ttcaccaaag tcgcgaccca | 1920 |
| ccgttccaag aacgtgcacc tgtaccgcca gggcgagatc aacctgatcc tcaacaacga | 1980 |
| gcccaacagc atcgcctcct actttgcggc cgaacacggc ccgtcggtgt gcggcatggc | 2040 |
| gttccgcgtg aaggactcgc aaaaggccta caaccgcgcc ctggaactcg gcgcccagcc | 2100 |
| gatccatatt gacaccgggc cgatggaatt gaacctgccg gcgatcaagg gcatcggcgg | 2160 |
| cgcgccgttg tacctgatcg accgtttcgg cgaaggcagc tcgatctacg acatcgactt | 2220 |
| cgtgtacctc gaaggtgtgg agcgcaatcc ggtcggtgca ggtctcaaag tcatcgacca | 2280 |
| cctgacccac aacgtctatc gcggccgcat ggtctactgg gccaacttct acgagaaatt | 2340 |
| gttcaacttc cgtgaagcgc gttacttcga tatcaagggc gagtacaccg gcctgacttc | 2400 |
| caaggccatg agtgcgccgg acggcatgat ccgcatcccg ctgaacgaag agtcgtccaa | 2460 |
| gggcgcgggg cagatcgaag agttcctgat gcagttcaac ggcgaaggca tccagcacgt | 2520 |
| ggcgttcctc accgacgacc tggtcaagac ctgggacgcg ttgaagaaaa tcggcatgcg | 2580 |
| cttcatgacc gcgccgccag acacttatta cgaaatgctc gaaggccgcc tgcctgacca | 2640 |
| cggcgagccg gtggatcaac tgcaggcacg cggtatcctg ctggacggat cttccgtgga | 2700 |
| aggcgacaaa cgcctgctgc tgcagatctt ctcggaaacc ctgatgggcc cggtgttctt | 2760 |
| cgaattcatc cagcgcaagg gcgacgatgg gtttggcgag tggaacttca aggcgctgtt | 2820 |

-continued

```
cgagtccatc gaacgtgacc aggtgcgtcg tggtgtattg accgccgatt aagcgtcaaa    2880
aagcccggcc gagggtgact cgacgaattt ccccgatcgt tcaaacattt ggcaataaag    2940
tttcttaaga ttgaatcctg ttgccggtct tgcgatgatt atcatataat ttctgttgaa    3000
ttacgttaag catgtaataa ttaacatgta atgcatgacg ttatttatga gatgggtttt    3060
tatgattaga gtcccgcaat tatacattta atacgcgata gaaaacaaaa tatagcgcgc    3120
aaactaggat aaattatcgc gcgcggtgtc atctatgtta ctagatcggg aattgcggcc    3180
gcaattcact ggccgtcgtt ttacaacgtc gtgactggga aaaccctggc gttacccaac    3240
ttaatcgcct tgcagcacat ccccctttcg ccagccagct gcattaatga atcggccaac    3300
gcgcggggag aggcggtttg cgtattgggc gctcttccgc ttcctcgctc actgactcgc    3360
tgcgctcggt cgttcggctg cggcgagcgg tatcagctca ctcaaaggcg gtaatacggt    3420
tatccacaga atcaggggat aacgcaggaa agaacatgtg agcaaaaggc cagcaaaagg    3480
ccaggaaccg taaaaaggcc gcgttgctgg cgttttttcca taggctccgc cccccctgacg    3540
agcatcacaa aaatcgacgc tcaagtcaga ggtggcgaaa cccgacagga ctataaagat    3600
accaggcgtt tccccctgga agctccctcg tgcgctctcc tgttccgacc ctgccgctta    3660
ccggatacct gtccgccttt ctcccttcgg gaagcgtggc gctttctcat agctcacgct    3720
gtaggtatct cagttcggtg taggtcgttc gctccaagct gggctgtgtg cacgaacccc    3780
ccgttcagcc cgaccgctgc gccttatccg gtaactatcg tcttgagtcc aacccggtaa    3840
gacacgactt atcgccactg gcagctgcca ctggtaacag gattagcaga gcgaggtatg    3900
taggcggtgc tacagagttc ttgaagtggt ggcctaacta cggctacact agaaggacag    3960
tatttggtat ctgcgctctg ctgaagccag ttaccttcgg aaaaagagtt ggtagctctt    4020
gatccggcaa acaaaccacc gctggtagcg gtggtttttt tgtttgcaag cagcagatta    4080
cgcgcagaaa aaaaggatct caagaagatc ctttgatctt ttctacgggg tctgacgctc    4140
agtggaacga aaactcacgt taagggattt tggtcatgag attatcaaaa aggatcttca    4200
cctagatcct tttaaattaa aaatgaagtt ttaaatcaat ctaaagtata tatgagtaaa    4260
cttggtctga cagttaccaa tgcttaatca gtgaggcacc tatctcagcg atctgtctat    4320
ttcgttcatc catagttgcc tgactccccg tcgtgtagat aactacgata cgggagggct    4380
taccatctgg ccccagtgct gcaatgatac cgcgagaccc acgctcaccg gctccagatt    4440
tatcagcaat aaaccagcca gctggaaggg ccgagcgcag aagtggtcct gcaactttat    4500
ccgcctccat ccagtctatt aattgttgcc gggaagctag agtaagtagt tcgccagtta    4560
atagtttgcg caacgttgtt gccattgcta caggcatcgt ggtgtcacgc tcgtcgtttg    4620
gtatggcttc attcagctcc ggttcccaac gatcaaggcg agttacatga tcccccatgt    4680
tgtgcaaaaa agcggttagc tccttcggtc ctccgatcgt tgtcagaagt aagttggccg    4740
cagtgttatc actcatggtt atggcagcac tgcataattc tcttactgtc atgccatccg    4800
taagatgctt ttctgtgact ggtgagtact caaccaagtc attctgagaa tagtgtatgc    4860
ggcgaccgag ttgctcttgc ccggcgtcaa tacgggataa taccgcgcca catagcagaa    4920
cttaaaagt gctcatcatt ggaaaacgtt cttcggggcg aaaactctca aggatcttac    4980
cgctgttgag atccagttcg atgtaaccca ctcgtgcacc cagctgatct tcagcatctt    5040
ttactttcac cagcgtttct gggtgagcaa aaacaggaag gcaaaatgcc gcaaaaaagg    5100
gaataagggc gacacggaaa tgttgaatac tcatactctt cctttttcaa tattattgaa    5160
gcatttatca gggttattgt ctcatgagcg gatacatatt tgaatgtatt tagaaaaata    5220
```

```
aacaaatagg ggttccgcgc acatttcccc gaaaagtgcc acctgacgcg ccctgtagcg    5280
gcgcattaag cgcggcgggt gtggtggtta cgcgcagcgt gaccgctaca cttgccagcg    5340
ccctagcgcc cgctcctttc gctttcttcc cttcctttct cgccacgttc gccggctttc    5400
cccgtcaagc tctaaatcgg gggctccctt tagggttccg atttagtgct ttacggcacc    5460
tcgaccccaa aaaacttgat tagggtgatg gttcacgtag tgggccatcg ccctgataga    5520 cggttttcg ccctttgacg ttggagtcca cgttctttaa tagtggactc ttgttccaaa     5580
ctggaacaac actcaaccct atctcggtct attcttttga tttataaggg attttgccga    5640
tttcggccta ttggttaaaa aatgagctga tttaacaaaa atttaacgcg aattttaaca    5700
aaatattaac gcttacaatt tccattcgcc attcaggctg cgcaactgtt gggaagggcg    5760
atcggtgcgg gcctcttcgc tattacgcca gctgatttaa atttaattaa ggcgcgccca    5820
tggatcgatg ttaacatgca tgatatcacg cgtggcgcca ctagtgctag cagatctggc    5880
cggcccaccg gtgggccata tgggcccgc                                      5909
```

USE OF HPPD INHIBITORS AS SELECTION AGENTS IN PLANT TRANSFORMATION

The present invention relates to the use of HPPD inhibitors as selection agents in the transformation of plant cells and of plants by genetic engineering. The transformation of plant cells and of plants by genetic engineering generally consists in introducing a foreign or heterologous gene encoding a protein of interest into the genome of the plant cells or of the plants which contain them. Once it has integrated into the genome of the plant cells, this heterologous gene is then expressed so as to confer on said cells and on said plants which contain them a novel characteristic related to the function of the heterologous gene which is expressed.

BACKGROUND OF THE INVENTION

Many techniques for transforming plant cells and plants by genetic engineering have been developed and thoroughly described in the literature. Firstly, methods which seek to introduce a DNA fragment carrying the heterologous gene in the form of "naked DNA" may be distinguished. This involves, in particular, bombarding cells, protoplasts or tissues with particles to which the DNA sequences are attached. Other methods may be used, such as microinjection or electroporation, or alternatively direct precipitation using PEG. Secondly, methods consisting in using, as a means of transfer into the plant, a heterologous chimeric gene in an agrobacterium tumefaciens Ti plasmid or an agrobacterium rhizogenes Ri plasmid will be distinguished. Those skilled in the art will choose the suitable method depending on the nature of the plant cell or of the plant to be transformed. Mention will in particular be made of the following Patents and Patent Applications: US 4,459,355, US 4,536,475, US 5,464,763, US 5,177,010, US 5,187,073, EP 267,159, EP 604 662, EP 672 752, US 4,945,050, US 5,036,006, US 5,100,792, US 5,371,014, US 5,478,744, US 5,179,022, US 5,565,346, US 5,484,956, US 5,508,468, US 5,538,877, US 5,554,798, US 5,489,520, US 5,510,318, US 5,204,253, US 5,405,765, EP 442 174, EP 486 233, EP 486 234, EP 539 563, EP 674 725, WO 91/02071 and WO 95/06128.

The methods for transforming plant cells generally comprise the following steps:

a) preparing competent plant cells capable of receiving the heterologous gene in a suitable medium, b) transforming the competent cells with the heterologous gene, c) growing and selecting the transformed cells comprising the heterologous gene in a suitable medium.

The competent plant cells may be embryogenic calluses, cell cultures on a solid support or in suspension, or embryogenic tissues, which are well known to those skilled in the art and widely described in the literature.

The production of transgenic plants, comprising the heterologous gene integrated into their genome, then consists in carrying out the following steps of:

d) regenerating plants from the transformed cells in one or more suitable media and, where appropriate, e) producing and recovering the seeds of the fertile transformed plants.

The pollination of the regenerated plants in order to produce the seeds of the fertile transformed plants takes place either by self-pollination or by cross-pollination with a nontransformed variety of the same plant or, optionally, with another variety which has stably integrated another heterologous gene into its genome.

The seeds of the transformed plants are then used in conventional selection programmes in order to produce novel varieties of transgenic plants which have stably integrated the heterologous gene into their genome. Such selection programmes are well known to those skilled in the art and comprise evaluating the agronomic properties of the plants produced and of their descendants, in particular with respect to the agronomic properties related to the expression of the heterologous gene.

The transformed cells are selected using a selection marker gene. Such marker genes and their use in transforming host organisms are well known to those skilled in the art and are widely described in the literature.

Among the genes encoding selection markers, mention may be made, firstly, of the genes encoding easily identifiable enzymes such as the GUS enzyme (or GFP, "Green Fluorescent Protein"), and genes encoding pigments or enzymes which regulate the production of pigments in the transformed cells. Mention will be made, secondly, of the genes for resistance to antibiotics and the genes for tolerance to herbicides (bialaphos, glyphosate or isoxazoles). In this case, the selection takes place by introducing into the medium suitable for the growth and selection of the transformed cells a selection agent of the antibiotic or herbicide type which is lethal for the nontransformed cells, only the cells comprising the gene for resistance to antibiotics or to herbicides being capable of growing on the selection medium. Such selection marker genes are in particular described in Patent Applications EP 242 236, EP 242 246, GB 2 197 653, WO 91/02071, WO 95/06128, WO 96/38567, WO 97/04103 or WO 99/24585.

The selection marker genes are introduced into the host cells simultaneously with the heterologous gene, either in the same vector, the two genes being associated in a convergent, divergent or colinear manner (WO 95/06128, U.S. Pat. No. 5,731,179), or in two vectors used simultaneously for transforming the plant cells. Under certain conditions (U.S. Pat. No. 5,731,179), and in particular when the heterologous gene and the selection marker gene are introduced separately in two vectors, simultaneously, the heterologous gene encoding a protein of interest and the selection marker gene may integrate on two different chromosomes in the genome of the transformed plant. It is possible, after recovering fertile transformed plants, to eliminate the marker gene in order to produce transformed plants comprising only the heterologous gene encoding a protein of interest. This elimination takes place by self-fertilization or by crossing the transformed plants comprising the heterologous gene and the selection marker gene with a nontransformed variety of the same plant, the segregation of the two genes occurring in conventional Mendelian fashion.

When the heterologous gene encoding a protein of interest is a herbicidal tolerance gene, the heterologous gene alone may be used as the selection marker in the process for transforming the plant cells or the plants.

The use of genes for tolerance to herbicides which are HPPD inhibitors, as selection markers in the processes for transforming plant cells and plants, has been described in the literature (WO 96/38567, WO 99/24585). The HPPD inhibitor is introduced into the culture medium of the cells after transformation (step c), in the same way as the other selection agents, according to the usual practices of those skilled in the art. HPPD inhibitors act on plant cells by inhibiting the synthesis of plastoquinones and of carotenoids. This action produces a bleaching of the plant cells which is not harmful to the growth of said cells, more particularly in the case of embryogenic tissues. Only the transformed plant cells comprising the gene for tolerance to HPPD inhibitors remain green and can be selected since they thus differ from the nontransformed cells.

SUMMARY OF THE INVENTION

The present invention consists in improving such a use in such a way as to facilitate the process for identifying and selecting the transformed cells. A second object of the present invention consists in decreasing the time required for selecting the transformed plants and for producing fertile regenerated plants. Specifically, the general process for transforming, selecting, regenerating and recovering the seeds of fertile transformed plants may take several months depending on the plants under consideration, about 10 to 18 months in particular for plants such as soya bean. Decreasing this duration by one or more months constitutes a definite technological and economical advantage.

The present invention consists in introducing the HPPD inhibitor into the culture medium of the competent plant cells (step a) so as to bleach said cells before the transformation step. The bleached competent cells are then transformed with the gene for tolerance to HPPD inhibitors, as a selection marker, and the transformed cells which have integrated said selection marker into their genome become green, enabling them to be selected. Such a process makes it possible to decrease the time required for selecting the transformed cells by several months, about 2 to 3 months.

The present invention therefore consists of a method for transforming plant cells by introducing a heterologous gene into said plant cells with a gene for tolerance to HPPD inhibitors as selection markers, said method comprising the steps of:

a) preparing and culturing competent plant cells capable of receiving the heterologous gene in a suitable medium, b) transforming the competent cells with the heterologous gene and the selection marker, c) growing and selecting the transformed cells comprising the heterologous gene in a suitable medium, characterized in that a step for bleaching the competent plant cells is carried out before the transformation step (b), by introducing a suitable amount of HPPD inhibitor into the suitable culture medium of the competent plant cells.

The present invention also consists in producing transgenic plants comprising the heterologous gene integrated into their genome, and then consists in carrying out the following steps of:

d) regenerating plants from the transformed cells selected in one or more suitable media and, where appropriate, e) producing and recovering the seeds of the fertile transformed plants.

Preferably, the transgenic plants produced using the method according to the invention are fertile transgenic plants.

DETAILED DESCRIPTION OF THE INVENTION

The plant cells according to the invention may be plant cells from monocotyledonous or dicotyledonous plants, more particularly crop plants which may or may not be intended for animal or human food, preferably dicotyledonous plants, in particular tobacco, rapeseed, sugarbeet, potatoes, cotton or soya bean, preferably soya bean.

The competent plant cells may be embryogenic calluses, cell cultures on a solid support or in suspension, or embryogenic tissues, which are well known to those skilled in the art and widely described in the literature. Advantageously, the competent plant cells are proliferative embryogenic tissues preferably maintained in a semi-solid medium (In Vitro Cell. Dev. Bioll. Plant 35 :451–455, 1999), and more particularly soya bean cells. The in vitro bleaching which is linked to the inhibition of tocopherol synthesis is not lethal and does not decrease cell division for these competent cells.

The present invention relates more particularly to a method for preparing a transgenic soya bean comprising a heterologous gene integrated into its genome, said method comprising the following steps:

a1) preparing proliferative embryogenic tissues by culturing immature zygotic soya bean embryos on a suitable inducer medium, a2) transferring the proliferative embryogenic tissues into a suitable culture medium, a3) bleaching the proliferative embryogenic tissues by adding a suitable amount of HPPD inhibitor to the culture medium, b) transforming the bleached proliferative embryogenic tissues by bombarding with particles coated with fragments of DNA comprising the heterologous gene and the gene for resistance to HPPD inhibitors, c) growing and selecting the transformed cells comprising the heterologous gene and the gene for resistance to HPPD inhibitors in a suitable culture medium comprising a suitable amount of HPPD inhibitor.

d) regenerating plants from the transformed cells selected on one or more suitable media, e) producing and recovering seeds of fertile transformed soya bean comprising the heterologous gene and the gene for resistance to HPPD inhibitors.

Advantageously, the HPPD inhibitors are chosen from isoxazoles (EP 418 175, EP 470 856, EP 487 352, EP 527 036, EP 560 482, EP 682 659, U.S. Pat. No. 5,424,276), in particular isoxaflutole, which is a herbicide selective for maize, diketonitriles (EP 496 630, EP 496 631), in particular 2-cyano-3-cyclopropyl-1-(2-CH3SO2-4-CF3 phenyl) propan-1,3-dione and 2-cyano-3-cyclopropyl-1-(2-CH3SO2-4-2,3-C12 phenyl)propan-1,3-dione, triketones (EP 625 505, EP 625 508, U.S. Pat. No. 5,506,195), in particular sulcotrione or mesotrione, and pyrazolinates. Preferably, the HPPD inhibitor is chosen from diketonitriles, in particular 2-cyano-3-cyclopropyl-1-(2-CH3SO2-4-CF3 phenyl) propan-1,3-dione and 2-cyano-3-cyclopropyl-1-(2-CH3SO2-4-2,3-C12 phenyl)propan-1,3-dione.

The suitable amount of HPPD inhibitor introduced into the suitable medium for preparing and culturing the competent cells according to the invention will depend, on the one hand, on the HPPD inhibitor used and, on the other hand, on the competent cells used, by virtue of their plant of origin and their form. Those skilled in the art will be able to determine this suitable amount using conventional techniques for growing the competent cells at various concentrations of the HPPD inhibitor used.

Preferably, the concentration of HPPD inhibitors is between 0.5 and 50 mg of active material per liter of medium, more preferably between 1 and 10 mg/l.

Advantageously, the HPPD inhibitor is applied to the competent plant cells in the culture medium between 1 month and 1 week before the transformation step, preferably between 15 and 10 days. Those skilled in the art will be able to determine the moment of application of the HPPD inhibitor before the transformation, depending on the tissues to be transformed and on the HPPD inhibitor and its concentration, and on the kinetics of bleaching the tissues. A common aspect of techniques for transforming plant cells is that the competent plant cells must be regularly subcultured in fresh culture media. The time between each subculturing will depend in particular on the culture medium and on the rate of growth of the plant cells. It is generally from 10 to 15 days. Advantageously, the HPPD inhibitor will be introduced into the fresh culture medium before subculturing the cells, generally in the course of the final subculturing prior to the transformation step.

The media suitable for preparing and culturing the competent plant cells, such as the media suitable for growing and selecting the transformed cells and the media for regenerating the transformed plants, are conventional media well known to those skilled in the art and widely described in the literature, and in particular the references cited in the present Patent Application.

According to a first embodiment of the invention, the medium suitable for preparing and culturing the competent plant cells and the medium suitable for growing and selecting the transformed cells are identical and comprise the same concentration of HPPD inhibitor. According to another embodiment of the invention, they differ only in their concentration of HPPD inhibitor, the first medium comprising a concentration of inhibitor which is higher than the second, or vice versa. According to another embodiment of the invention, the media differ in their composition of nutrient elements and hormones required for the growth of the competent cells before and after transformation. Preferably, the two media are identical in their composition of nutrient elements and hormones and their concentration of HPPD inhibitors.

According to a first embodiment of the invention, the medium suitable for preparing and culturing the competent cells and/or the medium suitable for growing and selecting the transformed cells is a D20 medium described by Santarem and Finer (In Vitro Cell. Dev. Biol.-Plant 35: 451–455, 1999), to which a suitable amount of HPPD inhibitor is added.

According to a second embodiment of the invention, the medium suitable for preparing and culturing the competent cells and/or the medium suitable for growing and selecting the transformed cells is an FNL medium described by Samoylov et al. (Plant Cell. Rep., 18 :49–54, 1998), the detailed composition of which is given in the examples hereinafter, to which a suitable amount of HPPD inhibitor is added. Preferably, the two media are FNL media.

The suitable inducer medium is preferably a D40 medium as defined in the examples.

The suitable regeneration medium is preferably an SBP6 medium described by Finer & Nagasawa (Plant Cell. Tissue and Organ Culture 15: 125–136, 1988), defined in the examples hereinafter for growing the tissues, then a medium as described by Finner & McMullen (In Vitro Cell. Dev. Biol. 27P :175–182, 1991) for converting the tissues to embryos, and then an MS medium, in particular an MS medium as described in the examples for germinating the embryos.

It is understood in the above and in the subsequent text that, when the heterologous gene, the introduction of which into the plant is desired, is a gene for tolerance to HPPD inhibitors, only the gene for resistance to HPPD inhibitors is introduced into the plant cells.

According to a preferential embodiment of the invention, the step for transforming the competent cells (step b) is carried out using the particle bombardment method, it being understood that other equivalent methods for transferring naked DNA, such as agitating the competent cells in the presence of DNA and of silica fibres (Whiskers), may be used. The principle of transformation by particle bombardment is well known to those skilled in the art and widely described in the literature for various species of plant cells and of plants. For transforming dicotyledonous plants, and soya bean in particular, mention will in particular be made of the following references: Finer et al. (Plant Cell. Rep. 11:323–328, 1992). Transformation by particle bombardment essentially consists in aggregating fragments of DNA comprising the genes to be transferred, on metal particles which are then bombarded onto the competent plant cells using particle guns. The particles, like the machines, which allow the bombardment of the competent cells are well known to those skilled in the art, described in the literature and commercially available. Mention will in particular be made of Patents and Patent Applications U.S. Pat. No. 4,945,050, EP 270 356, U.S. Pat. No. 5,204,253, EP 434 616, U.S. Pat. No. 5,516,670, EP 535 005 and U.S. Pat. No. 5,466,587. According to a preferential embodiment of the invention, the metal particles are particles functionalized by grafting aminated silicones as described in U.S. Pat. No. 6,068,980.

Preferably, the genes for tolerance to HPPD inhibitors comprise, in the direction of transcription, a regulatory promoter sequence which is functional in plant cells and plants, functionally linked to a DNA sequence encoding an HPPD, functionally linked to a regulatory terminator sequence which is functional in plant cells and plants. The sequences encoding HPPDs are native HPPD sequences, in particular from plants, from microorganisms, from fungi or from mammals, in particular the sequences described in Patent Applications WO 96/38567, U.S. Pat. No. 6,087,563, WO 97/49816 and WO 99/24585. They are in particular sequences encoding HPPDs from *Pseudomonas fluroescens*, from *Arabidopsis thaliana*, from carrot, from wheat or from Synecocistys. The sequences encoding HPPDs are also sequences mutated in their C-terminal portion as described in Patent Application WO 99/24585 or chimeric HPPDs as described in Patent Application WO 99/24586. According to a preferential embodiment of the invention, the DNA sequence encoding an HPPD is an HPPD sequence mutated in its terminal portion, more particularly a sequence comprising the W336 mutation as described in Patent Application WO 99/24585, more preferably the HPPD sequence from *Pseudomonas fluorescens*. comprising the W336 mutation as described in Patent Application WO 99/24585.

Figure 1:
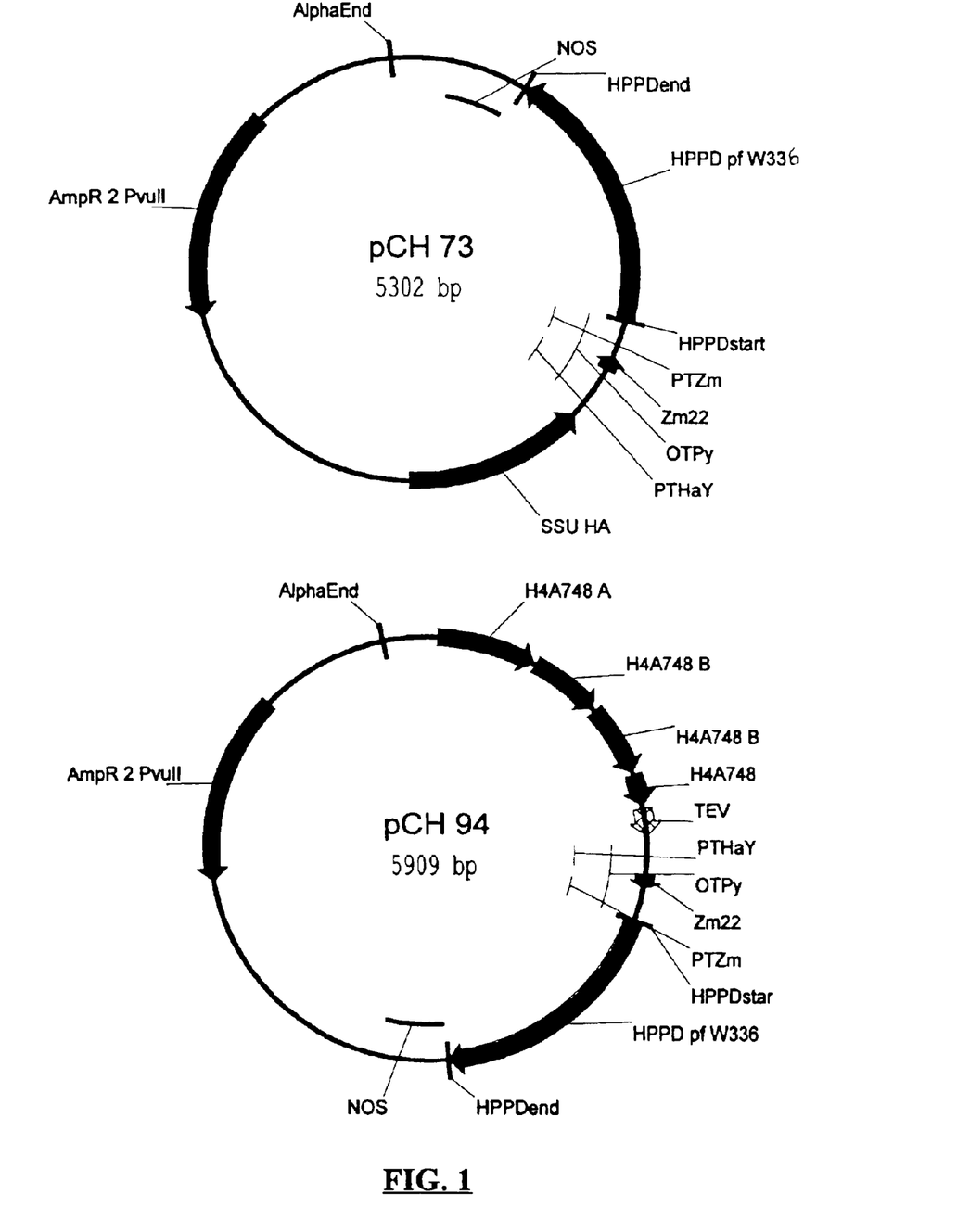
FIG. 1 shows maps of the plasmids pCH 73 and pCH 94.

According to a preferential embodiment of the invention, the gene for tolerance to HPPD inhibitors comprises, in the direction of transcription, a regulatory promoter sequence selected from the promoter of the RuBisCo small subunit from sunflower, described in Patent Application WO 99/25842, or the histone promoter from *Arabidopsis thaliana* combined with the tobacco etch virus (TEV) enhancer as described in Patent Application WO 99/24585, functionally linked to a DNA sequence encoding a transit peptide, preferably an optimized transit peptide, as defined hereinafter, functionally linked to a DNA sequence encoding an HPPD as defined above, preferably a sequence encoding an HPPD from *Pseudomonas fluorescens*, comprising the W336 mutation, functionally linked to a regulatory terminator sequence, in particular the NOS terminator sequence defined hereinafter. The corresponding genes for tolerance to HPPD inhibitors are represented, in the attached figures, by the maps of plasmids pCH73 and pCH94 and by their nucleotide sequences:

pCH73 : SEQ ID NO 1, 3'–5' representation
Promoter: 4541–5257
Optimized transit peptide: 4130–4487
HPPDW336: 3045–4119
NOS: 2749–3000

PCH94: SEQ ID NO 2
Promoter: 34–1272
TEV enhancer: 1292–1421
Optimized transit peptide: 1428–1793
HPPDW336: 1795–2869
NOS: 2914–3165.

Preferably, the heterologous genes encoding a protein of interest comprise, in the direction of transcription, a regulatory promoter sequence which is functional in plant cells and plants, functionally linked to a DNA sequence encoding a protein or a peptide of interest, functionally linked to a regulatory terminator sequence which is functional in plant cells and plants.

The DNA sequences encoding a protein or a peptide of interest are generally sequences encoding proteins or peptides which confer, on the transformed plant, novel agronomic properties or improvement of the agronomic quality of the transformed plant.

Among the genes which confer novel agronomic properties on the transformed plants, mention may be made of the DNA sequences encoding proteins which confer tolerance to certain herbicides, those which confer resistance to certain insects, those which confer tolerance to certain diseases, etc. Such genes are in particular described in Patent Applications WO 91/02071 and WO 95/06128.

Among the DNA sequences encoding proteins which confer tolerance to certain herbicides on the transformed plant cells and plants, mention may be made of the Bar gene which confers tolerance to bialaphos, the gene encoding a suitable EPSPS which confers resistance to herbicides having EPSPS as a target, such as glyphosate and its salts (U.S. Pat. Nos. 4,535,060, US 4,769,061, US 5,094,945, US 4,940,835, US 5,188,642, US 4,971,908, US 5,145,783, US 5,310,667, US 5,312,910, US 5,627,061, US 5,633,435, FR 2 736 926), the gene encoding glyphosate oxydoreductase (U.S. Pat. No. 5,463,175), or a gene encoding an HPPD which confers tolerance to the herbicides which have HPPD as a target and which are cited above, such as isoxazoles, in particular isoxafutole (FR 95 06800, FR 95 13570), diketonitriles (EP 496 630, EP 496 631) or triketones, in particular sulcotrione or mesotrione (EP 625 505, EP 625 508, U.S. Pat. No. 5,506,195).

Among the DNA sequences encoding a suitable EPSPS which confer resistance to the herbicides which have EPSPS as a target, mention will more particularly be made of the gene which encodes a plant EPSPS, in particular maize EPSPS, which has two mutations, 102 and 106, and which is described in Patent Application FR 2 736 926, hereinafter named EPSPS double mutant, or the gene which encodes an EPSPS isolated from agrobacterium and which is described by sequence ID No. 2 and sequence ID No. 3 of U.S. Pat. No. 5,633,435, hereinafter named CP4.

In the cases of the DNA sequences encoding EPSPS or HPPD, and more particularly encoding the genes above, the sequence encoding these enzymes is advantageously preceded by an sequence encoding a transit peptide, in particular encoding the "optimized transit peptide" described in U.S. Pat. Nos. 5,510,471 or 5,633,448.

Among the DNA sequences encoding proteins of interest which confer novel properties of resistance to insects, mention will more particularly be made of the Bt proteins widely described in the literature and well known to those skilled in the art. Mention will also be made of proteins extracted from bacteria such as Photorabdus (WO 97/17432 & WO 98/08932).

Among the DNA sequences encoding proteins or peptides of interest which confer novel properties of resistance to diseases, mention will in particular be made of chitinases, glucanases and oxalate oxidase, all these proteins and their coding sequences being widely described in the literature, or antibacterial and/or antifungal peptides, in particular peptides of less than 100 amino acids which are rich in cysteines, such as plant thionins or defensins, and more particularly lytic peptides of any origin comprising one or more disulphide bridges between the cysteines and regions comprising basic amino acids, in particular the following lytic peptides: androctonin (WO 97/30082 and WO 99/09189), drosomycin (WO 99/02717), thanatin (WO 99/24594) or heliomycin (WO 99/53053). According to a particular embodiment of the invention, the protein or peptide of interest is chosen from fungal elicitor peptides, in particular elicitins (Kamoun et al., 1993; Panabieres et al., 1995).

Among the DNA sequences encoding proteins or peptides which modify the constitution of the modified plants, mention may be made, in particular, of the DNA sequences encoding proteins or peptides which modify in particular the content and the quality of certain essential fatty acids (EP 666 918) or the content and the quality of the proteins, in particular in the leaves and/or the seeds of said plants. Mention will in particular be made of the genes encoding proteins enriched in sulphur-containing amino acids (Korit, A. A. et al., Eur. J. Biochem. (1991) 195, 329–334 ; WO 98/20133 ; WO 97/41239 ; WO 95/31554 ; WO 94/20828 ; WO 92/14822). Theses proteins enriched in sulphur-containing amino acids will also have the function of trapping and storing excess methionine and/or cysteine, making it possible to avoid the possible problems of toxicity which are linked to an overproduction of these sulphur-containing amino acids, by trapping them. Mention may also be made of the genes encoding peptides rich in sulphur-containing amino acids and more particularly in cysteines, said peptides also having antibacterial and/or antifungal activity. Mention will more particularly be made of plant defensins, as well as lytic peptides of any origin, and more particularly the lytic peptides previously described. Mention will also be made of the SAT proteins described in Patent Applications WO 00/36127, WO 00/04167 and WO 00/01833.

As a regulatory sequence which is a promoter in plant cells and plants, use may be made of any promoter sequence of a gene which is naturally expressed in plants, in particular a promoter which is expressed especially in the leaves of plants, such as for example "constitutive" promoters of bacterial, viral or plant origin, or "light-dependent" promoters, such as that of a plant ribulose-biscarboxylase/oxygenase (RuBisCO) small subunit gene, or any suitable known promoter which may be used. Among the promoters of plant origin, mention will be made of the histone promoters as described in Application EP 0 507 698, or the rice actin promoter (U.S. Pat. No. 5,641,876). Among the promoters of a plant virus gene, mention will be made of that of the cauliflower mosaic virus (CAMV 19S or 35S), or the circovirus promoter (AU 689 311).

Use may also be made of a regulatory promoter sequence specific for particular regions or tissues of plants, and more particularly promoters specific for seeds ([22] Datla, R. et al., Biotechnology Ann. Rev. (1997) 3, 269–296), especially the napin promoter (EP 255 378), the phaseolin promoter, the glutenin promoter, the helianthinin promoter (WO 92/17580), the albumin promoter (WO 98/45460), the oelosin promoter (WO 98/45461), the SATI promoter or the SAT3 promoter (PCT/U.S. Pat. No. 98/06978, filed on Oct. 20, 1998, incorporated herein by way of reference).

Use may also be made of an inducible promoter advantageously chosen from the phenylalanine ammonia lyase (PAL), HMG-CoA reductase (HMG), chitinase, glucanase, proteinase inhibitor (PI), PRI family gene, nopaline synthase (nos) and vspB promoters (U.S. Pat. No. 5,670,349, Table 3), the HMG2 promoter (U.S. Pat. No. 5,670,349), the apple beta-galactosidase (ABG1) promoter and the apple aminocyclopropane carboxylate synthase (ACC synthase) promoter (WO 98/45445).

According to the invention, use may also be made, in combination with the promoter, other regulatory sequences, which are located between the promoter and the coding sequence, such as transcription activators ("enhancers"), for instance the translation activator of the tobacco mosaic virus (TMV) described in Application WO 87/07644, or of the tobacco etch virus (TEV) described by Carrington & Freed, for example, or introns such as the adhl intron of maize or intron 1 of rice actin.

As a regulatory terminator or polyadenylation sequence, use may be made of any corresponding sequence of bacterial origin, such as for example the nos terminator of Agrobacterium tumefaciens, of viral origin, such as for example the CaMV 35S terminator, or of plant origin, such as for example a histone terminator as described in Application EP0 633 317.

The sequences encoding an HPPD, like the sequences encoding a protein or peptide of interest, may comprise functionally linked in 5' or in 3', sequence encoding signals for targeting into various compartments of the plant cell, such as chloroplasts, mitochondria or the vacuole. Such signals are described in the literature and are well known to those skilled in the art. The chloroplast transit peptides may be simple, such as an EPSPS transit peptide (U.S. Pat. No. 5,188,642) or a plant ribulose-biscarboxylase/oxygenase small subunit (RuBisCO ssu) transit peptide, optionally comprising some amino acids of the N-terminal portion of the mature RuBisCO ssu (EP 189 707), or a multiple transit peptide comprising a first plant transit peptide fused to a portion of the N-terminal sequence of a mature protein located in the plastid, fused to a second plant transit peptide as described in Patent EP 508 909, and more particularly the optimized transit peptide comprising a sunflower RuBisCO ssu transit peptide fused to 22 amino acids of the N-terminal end of maize RuBisCO ssu fused to the maize RuBisCO ssu transit peptide as described with its coding sequence in Patent EP 508 909.

The examples hereinafter make it possible to illustrate the invention for the transformation of soya bean, without, however, seeking to limit the scope thereof.

All the methods or procedures described below in these examples are given by way of examples and correspond to a choice made from the various methods available in order to attain the same result. Most of the methods for engineering DNA fragments are described in "Current Protocols in Molecular Biology" Volumes 1 and 2, Ausubel F.M. et al., published by Greene Publishing Associates and Wiley-Interscience (1989) or in Molecular cloning, T. Maniatis, E. F. Fritsch, J. Sambrook,1982.

The content of all the references cited in the description above and in the examples hereinafter is incorporated into the contents of the present Patent Application by way of reference.

EXAMPLE 1

Technology for Transforming Soya Bean

The technology used for transforming soya bean has been described by Santarem & Finer: Transformation of soya bean (Glycine max (L.) Merrill) using proliferative embryogenic tissue maintained on semi-solid medium. In Vitro Cell. Dev. Biol. Plant 35 451–455, 1999. It comprises the steps hereinafter.

Immature zygotic embryos (from 3 to 4 mm) are aseptically dissected and placed with the adaxial side upwards in a medium comprising 2.4D (D40).

D 40 is a Murashige and Skoog medium described in: Murashige & Skoog: A revised medium for rapid growth and bioassays with tobacco tissue cultures. Physiol. Plant. 15 : 473–497; 1962: $NH_4NO_3$:1650 mg/l; $H_3BO_3$:6.2 mg/l; $CaCl_2.2H_2O$: 332.2 mg/l; $CoCl_2.6H_2O$: 0.025 mg/l; $CuSO_4.5H_2O$: 0.025 mg/l; $Na_2EDTA$: 37.26 mg/l; $FeSO_4.7H_2O$: 27.8 mg/l; $MnSO_4.7H_2O$:16.9 mg/l; $Na_2MoO_4.2H_2O$: 0.25 mg/l; KI: 0.83 mg/l; $KNO_3$: 1 900 mg/l; $KH_2PO_4$:170 mg/l; $ZnSO_4.7H_2O$: 8.6 mg/l, with Gamborg B5 vitamin mix described by: Gamborg, Miller and Ojima: Nutrient requirements of suspension cultures of soya bean root cells. Exp. Cell Res. 50 : 151–158, 1968: myo-inositol: 100 mg/l; nicotinic acid: 1 mg/l; pyridoxine-HCl: 1 mg/l; thiamine-HCl: 10 mg/l; 40 mg/l of 2.4-D and 6% sucrose; 0.3% gelrite, pH 7.0.

After culturing for 3 weeks in D40 medium, the cotyledons are transferred onto a D20 medium which comprises essentially the same elements as the D40 medium, with the exception of the 2.4D concentration, which is decreased to 20 mg/l, and the sucrose concentration, which is decreased from 60 g/l to 30 g/l, at pH 5.7.

On this medium, the somatic embryos begin to proliferate in the form of compact aggregates or clumps. The embryogenic clumps are then transferred every two weeks onto a new D20 medium in order to increase the production of tissues. Five or six transfers (approximately 3 months) onto this medium are necessary in order to optimize their competence at transformation. The use of embryogenic tissues which are at an earlier stage produces much poorer results.

Transformation of Tissues

Particle bombardment is used for transforming the embryogenic tissues.

Particle preparation: flnctionalized tungsten (M17) particles are prepared according to U.S. Pat. No. 6,068,980. The particles are functionalized by grafting aminated silicones as the vectorization element, and washed in absolute ethanol. 2.5 mg of particles in ethanol are mixed with 3 µg of DNA. After precipitation, the particles are pipetted and used for two shots with a particle gun of the PIG type described by Finer, Vain, Lones and McMullen in: Development of the Particle Inflow Gun for DNA delivery to plant cells. Plant Cell Rep. 11: 323–328, 1992.

Before the bombardment, the tissues are dried under vacuum under a laminar-flow hood for 5 to 10 min, and then placed between two 500 µm screens and bombarded twice.

After the bombardment, the tissues are transferred twice onto D20 (2×10 days) before beginning the selection with hygromycin (30 mg/l).

In order to avoid handling tissues and to gain time, the bombarded calluses are placed on a sterile gauze screen fixed with two metal rings (FIG. 2) which enable direct contact between the embryogenic tissues and the solid medium. The gauze screens are transferred onto fresh media every 15 days until green calluses are observed. It is understood that the principle of callus transfer described above is not limited to soya bean calluses and to selection with hygromycin, but may be used for any method for culturing tissues and cell suspensions which requires frequent changing of culture medium.

Amplification and Regeneration of Tissues

The green calluses which grow on medium comprising hygromycin are amplified for 1 month on SBP6 medium described by Finer & Nagasawa in: Development of an embryogenic suspension culture of soya bean (Glycine max Merill.) Plant Cell. Tissue and Organ Culture 15: 125–136, 1988: $Na_2EDTA$: 37.24 mg/l; $FeSO_4.7H_2O$: 27.84 mg/l: $MgSO_4.7H_2O$: 370 mg/l; $MnSO_4.H_2O$: 16.9 mg/l; $ZnSO_4.H_2O$: 8.6 mg/l; $CuSO_4.7H_2O$: 0.025 mg/l, $CaCl_2.2H_2O$: 440 mg/l; KI: 0.83 mg/l; $CoCl_2.6H_2O$: 0.025 mg/l; $KH_2PO_4$: 170 mg/l; $H_3BO_3$: 6.2 mg/l; $Na_2MoO_4.2H_2O$: 0.25 mg/l; myo-inositol: 100 mg/l: nicotinic acid: 1 mg/l; pyridoxine-HCl: 1 mg/l; thiamine-HCl: 10 mg/l; $NH_4NO_3$: 800 mg/l; $KNO_3$: 3 000 mg/l; asparagine: 670 mg/l; 6% sucrose; 2.4-D: 5 mg/l, pH 5.7.

When sufficient tissues have been produced, they are then converted to embryos using a medium described by Finer & McMullen in: Transformation of soya bean via particle bombardment of embryogenic suspension culture tissue. In Vitro Cell. Dev. Biol. 27P: 175–182, 1991.

After 3–4 transfers onto this medium, the embryos are air-dried in a Petri dish for 2 days before germination on a Murashige & Skoog medium (B5 vitamins) at half strength with 15 g/l of sucrose and 7 g/l of phytagar, pH 5.7.

When the plants are well developed, they are transferred into a "jiffy pot" peat-based substrate for a period of 10 days in order to acclimatize before being transferred under glass.

This technology using the gauze screen and selection with hygromycin makes it possible to regenerate 200 calluses per person and per year.

EXAMPLE 2

Transformation of the Tissues According to the Invention

The same selection method was developed for the HPPD inhibitors, with a D20 medium comprising 2 mg/l of isoxaflutole or 0.5 to 5 mg/l of diketonitriles. The gene for tolerance to HPPD inhibitors which was used as a selection marker is pCH73 or pCH94 represented in FIG. 1.

In order to avoid handling tissues and to gain time, the bombarded calluses are placed on sterile gauze screen fixed with two metal rings which enable direct contact between the embryogenic tissues and the solid medium. The gauze screens are transferred onto fresh media every 15 days until green calluses are observed. It is understood that the principle of callus transfer described above is not limited to soya bean calluses and to selection with hygromycin, but may be used for any method for culturing tissues and cells suspensions which requires frequent changing of culture medium.

10 to 15 days prior to the bombardment, the isoxaflutole or the diketonitriles are introduced into the D20 medium, at the abovementioned concentrations, so as to bleach the tissues. After bombardment, the tissues are placed directly in the same D20 medium comprising 2 mg/ml of isoxaflutole or diketonitrile (between 0.5 and 5 mg/l) and transferred into fresh medium every 15 days. After 4 transfers onto the isoxaflutole. green calluses are identified and amplified as described in Example 1. The time required for producing calluses of cells which are competent for the bombardment is 3 and a half months. The selection of the transformed cells (green calluses) occurs approximately 6 months after the initiation of the calluses for the transformation.

When the tissues are transferred for selection on the isoxaflutole, they are rapidly bleached by the herbicide, without any inhibition of growth being observed. This is due to the fact that the absence of carotenoids, of chlorophyll and of tocopherols is not essential to the growth of tissues.

The results obtained with and without prior bleaching are represented in Table 1 hereinafter.

TABLE 1

| | Transformation on D20 medium | | | | | |
|---|---|---|---|---|---|---|
| Bleaching | pCH73 | | | pCH94 | | |
| Attempt | 1 | 2 | 3 | 1 | 2 | 3 |
| Before bombardment | 0 | 0.5 | 0.25 | 0.67 | 1 | 2 |
| After bombardment | 0 | 0 | 0.25 | 0.67 | 0.33 | 0.25 |

They show, in particular for pCH94, a greater number of calluses identified when initiating the selection before the bombardment according to the invention. This greater number of calluses selected is linked to the improvement of the selection process according to the invention by facilitating the identification of the transformed calluses.

EXAMPLE 3

Choice of Medium

In order to improve the selection process according to the invention, an attempt was made to decrease the number of tissue transfers and the time required for producing calluses of competent cells and green calluses selected after bombardment. To this effect, the D20 medium previously used was replaced with a modified FNL medium which allows rapid proliferation of the tissues.

The FNL medium has been described by Samoylov, Tucker, Thibaud-Nissen & Parrott in: A liquid-medium-based protocol for rapid regeneration from embryogenic soya bean cultures: Plant Cell Rep, 18: 49–54, 1998.

This medium makes it possible to produce tissues ready for bombardment more rapidly, greater embryogeny and shorter transfer cycles.

Composition of the FNL medium: Na2EDTA: 37.24 mg/l; $FeSO_4$, $7H_2O$: 27.84 mg/l; $MgSO_4$, $7H_2O$: 370 mg/l; $MnSO_4$. $H_2O$: 16.9 mg/l; $ZnSO_4$, $H_2O$: 8.6 mg/l; $CuSO_4$. $7H_2 5O$: 0.025 mg/l; $CaCl_2$. $2H_2O$: 440 mg/l; KI: 0.83 mg/l; $CoCl_2$. $6H_2O$: 0.025 mg/l; $KH_2PO_4$: 170 mg/l; $H_3BO_3$: 6.2 mg/l; $Na_2MoO_4$. $2H_2O$: 0.25 mg/l; myo-inositol: 100 mg/l; nicotinic acid: 1 mg/l; pyridoxine-HCl: 1 mg/l; thiamine-HCl: 10 mg/l; $(NH_4)_2SO_4$: 460 mg/l; $KNO_3$: 2820 mg/l; asparagine: 670 mg/l; 1% sucrose; 2.4-D: 10 mg/l; 0.3% gelrite; pH 5.7.

However, in the absence of prior bleaching, the amount of tissues to be manipulated during the selection process remains too great, comparable to that of the D20 medium due to the considerable rate of the development.

The bombardment of tissues bleached with isoxaflutol according to the invention requires only one transfer of calluses before the selected green calluses are produced, against 4 when using the D20 medium.

The time required for producing calluses from cells which are competent for the bombardment is 2 months, the transformed green calluses being selected approximately 3 months after the initiation of the calluses for transformation.

The results of transformation with the plasmides pCH73 and pCH94 are given in Table 2 hereinafter.

TABLE 2

| | Transformation on FNL medium | | | | | | |
|---|---|---|---|---|---|---|---|
| Bleaching | pCH73 | | | PCH94 | | | |
| Attempt | 1 | 2 | 3 | 1 | 2 | 3 | 4 |
| Before bombardment | 1 | 1.5 | 0.33 | 1 | 1 | 0.33 | 1.5 |
| After bombardment | 0.25 | 0 | — | — | — | — | — |

The mean number of green calluses selected per transformation trial when using the bleached tissues according to the invention is 1 per shot. This table also shows that, with prior bleaching of the tissues, the same transformation frequencies are produced for the two genes pCH73 and pCH94, whereas the RuBisCo ssu promoter of pCH73 is known to be weakly expressed in calluses in vitro, unlike the histone promoter of pCH94.

Figure 2:
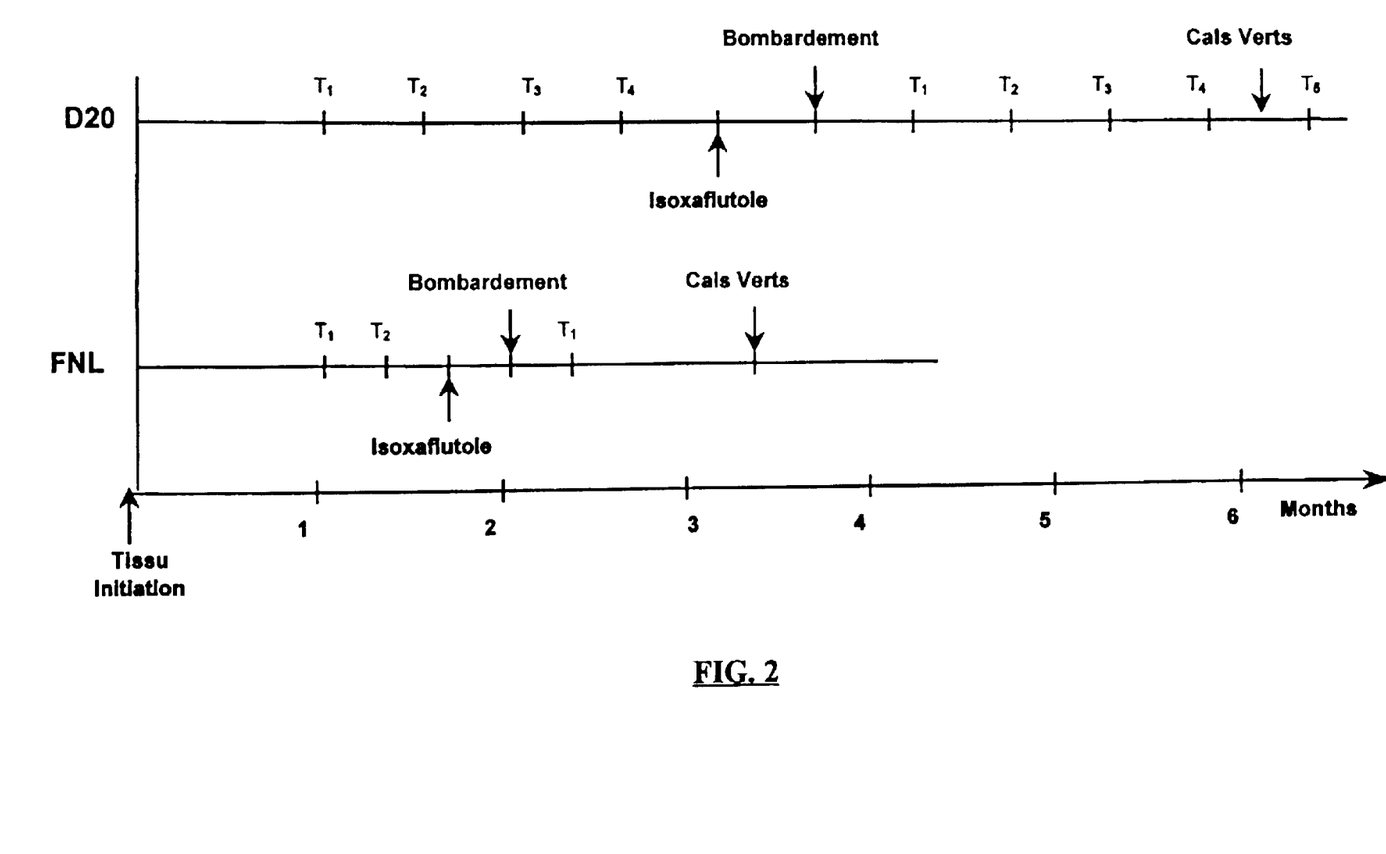
FIG. 2 shows results of the choice of medium (D20 and FNL) on decreasing the time needed for the production of calluses of competent cells and green calluses selected after bombardment.

The use of the FNL medium in combination with the prior bleaching of the tissues according to the invention makes it possible to substantially decrease the time required for selecting the green calluses and the work load for the entire process of transforming the plants (FIG. 2).

What is claimed is:

1. Method for transforming plant cells by introducing a heterologous gene into said plant cells with a gene for tolerance to HPPD inhibitors as a selection marker, said method comprising the steps of:
   (a) preparing and culturing competent plant cells capable of receiving the heterologous gene and selection marker in a suitable medium, wherein said competent plant cells are embryogenic calluses or embryogenic tissues,
   (b) bleaching the competent plant cells by introducing a suitable amount of HPPD inhibitor into the suitable medium of the competent plant cells,
   (c) transforming the competent cells with the heterologous gene and the selection marker, (d) growing and selecting the transformed cells comprising the heterologous gene and the selection marker in a suitable medium wherein transformed cells appear green indicating the presence in the transformed cells of the heterologous gene and selection marker,
   wherein said gene for tolerance to HPPD inhibitors comprises, in the direction of transcription, a regulatory promoter sequence which is functional in plant cells and plants, functionally linked to a DNA sequence encoding an HPPD, functionally linked to a regulatory terminator sequence which is functional in plant cells and plants.

2. Method for preparing transgenic plants comprising a heterologous gene integrated into their genome, comprising a method for transforming plant cells according to claim 1, and further comprising the following steps of:
   e) regenerating plants from the transformed cells selected in one or more suitable media and, where appropriate,
   f) producing and recovering seeds of the fertile transformed plants, said seeds comprising the heterologous gene and the selection marker.

3. Method according to claim 2, characterized in that the transgenic plants produced using the method according to the invention are fertile transgenic plants.

4. Method according to claim 1, characterized in that the plant cells are chosen from the cells of dicotyledonous plants.

5. Method according to claim 4, characterized in that the plant cells are soya bean cells.

6. Method according to claim 1, characterized in that the competent plant cells are proliferating embryogenic tissues.

7. Method according to claim 6, characterized in that the proliferating embryonic tissues are maintained in a semi-solid medium.

8. Method according to claim 7, characterized in that the semi-solid medium is an FNL medium.

9. Method according to claim 1, characterized in that the HPPD inhibitor is chosen from isoxazoles, diketonitriles, triketones, and pyrazolinates.

10. Method according to claim 9, characterized in that the concentration of HPPD inhibitors is between 0.5 mg/ml and 50 mg/ml.

11. Method for preparing transgenic plants comprising a heterologous gene integrated into their genome, which method comprises a method for transforming plant cells by introducing a heterologous gene into said plant cells with a gene for tolerance to HPPD inhibitors as a selection marker, said method comprising the steps of:
   a) preparing and culturing competent plant cells capable of receiving the heterologous gene and the selection marker in a suitable medium,
   b) bleaching the competent plant cells by introducing a suitable amount of HPPD inhibitor into the suitable culture medium of the competent plant cells,
   c) transforming the competent cells with the heterologous gene and the selection marker,
   d) growing and selecting the transformed cells comprising the heterologous gene and the selection marker in a suitable medium wherein transformed cells appear green indicating the presence in the transformed cells of the heterologous gene and selection marker,
   e) regenerating plants from the transformed cells selected in one or more suitable media and, where appropriate,
   f) producing and recovering seeds of the fertile transformed plants, said seeds comprising the heterologous gene and the selection marker, then producing novel varieties of transgenic plants which have stably integrated the heterologous gene into their genome, in conventional selection programmes, wherein said gene for tolerance to HPPD inhibitors comprises, in the direction of transcription, a regulatory promoter sequence which is functional in plant cells and plants, functionally linked to a DNA sequence encoding an HPPD, functionally linked to a regulatory terminator sequence which is functional in plant cells and plants.

12. Method according to claim 2, characterized in that the selection marker gene is eliminated by crossing the transformed plants comprising the heterologous gene and the selection marker gene with a nontransformed variety of the same plant.

13. Method according to claim 4, characterized in that the plant cells are chosen from the cells of tobacco, rapeseed, sugar beet, potatoes, cotton and soya bean.

14. Method according to claim 9, characterized in that the HPPD inhibitor is isoxaflutole.

15. Method according to claim 9, characterized in that the HPPD inhibitor is 2-cyano-3-cyclopropyl-1-1(2-CH3SO2-4-CF3 phenyl)propan-1,3-dione or 2-cyano-3-cyclopropyl 1-1-(2-CH3SO2-4-2-C12 phenyl)propan-1,3-dione.

16. Method according to claim 9, characterized in that the HPPD inhibitor is sulcotrione or mesotrione.

17. Method according to claim 10, characterized in that the concentration of inhibitors is between 1 mg/ml and 10 mg/ml.

* * * * *